(12) United States Patent
Zhu et al.

(10) Patent No.: US 10,441,499 B1
(45) Date of Patent: Oct. 15, 2019

(54) ACOUSTIC SHOCK WAVE DEVICES AND METHODS FOR GENERATING A SHOCK WAVE FIELD WITHIN AN ENCLOSED SPACE

(71) Applicant: S-WAVE MEDICAL INC., Foster City, CA (US)

(72) Inventors: Da Zhu, Foster City, CA (US); Zhuoyu Chen, Foster City, CA (US)

(73) Assignee: S-WAVE CORP., Foster City, CA (US)

( * ) Notice: Subject to any disclaimer, the term of this patent is extended or adjusted under 35 U.S.C. 154(b) by 0 days.

(21) Appl. No.: 16/164,702

(22) Filed: Oct. 18, 2018

(51) Int. Cl.
*A61H 23/00* (2006.01)
*A61B 17/225* (2006.01)
*G10K 15/04* (2006.01)
*A61H 23/02* (2006.01)

(52) U.S. Cl.
CPC ....... *A61H 23/008* (2013.01); *A61B 17/2251* (2013.01); *A61H 23/0245* (2013.01); *G10K 15/043* (2013.01); *A61B 2017/2253* (2013.01); *A61H 2201/1645* (2013.01)

(58) Field of Classification Search
CPC .............. A61H 23/008; A61H 23/0245; A61H 2201/1645; A61B 17/2251; A61B 2017/2253; G10K 15/043
See application file for complete search history.

(56) References Cited

U.S. PATENT DOCUMENTS

| | | | |
|---|---|---|---|
| 2,559,227 A | 7/1951 | Rieber | |
| 4,539,989 A | 9/1985 | Forssmann et al. | |
| 5,119,801 A | 6/1992 | Eizenhoefer et al. | |
| 5,174,280 A | 12/1992 | Gruenwald et al. | |
| 5,224,468 A | 7/1993 | Grunewald et al. | |
| 5,941,838 A | 8/1999 | Eizenhofer | |
| 6,869,407 B2* | 3/2005 | Ein-Gal | G10K 15/043 600/439 |
| 7,507,213 B2 | 3/2009 | Schultheiss et al. | |
| 7,527,589 B2* | 5/2009 | Squicciarini | A61F 2/26 600/39 |
| 7,601,127 B2 | 10/2009 | Schultheiss et al. | |
| 7,841,995 B2 | 11/2010 | Schultheiss et al. | |
| 7,988,648 B2 | 8/2011 | Warlick et al. | |
| 8,162,859 B2 | 4/2012 | Schultheiss et al. | |
| 8,257,282 B2 | 9/2012 | Uebelacker et al. | |
| 9,381,380 B2 | 7/2016 | Ein-Gal | |
| 9,913,748 B2 | 3/2018 | Spector et al. | |

(Continued)

*Primary Examiner* — Boniface N Nganga
(74) *Attorney, Agent, or Firm* — Morrison & Foerster LLP (57) ABSTRACT

Devices and methods for generating acoustic shock wave within a cavity is disclosed. The shock wave device optionally includes a housing having a cylindrical portion and a cone frustum portion. The housing optionally forms a cavity configured to receive a body appendage. The shock wave device optionally includes a plurality of shock wave generators and a coupling assembly having a deformable sac configured to hold shock wave transmitting liquid. The volume of the transmitting liquid is optionally increased or decreased as needed so that the coupling assembly can conform to the shape of the body appendage. The shock waves generated optionally has an intensity gradient within the cavity of the shock wave device, where the intensity gradient is optionally controllable using a control and power supply unit.

22 Claims, 8 Drawing Sheets

(56) References Cited

U.S. PATENT DOCUMENTS

| | | | |
|---|---|---|---|
| 2007/0239074 A1* | 10/2007 | Ein-Gal | A61B 17/2251 |
| | | | 601/2 |
| 2012/0215142 A1* | 8/2012 | Spector | A61B 17/2251 |
| | | | 601/46 |
| 2012/0253240 A1 | 10/2012 | Uebelacker et al. | |
| 2015/0073312 A1* | 3/2015 | Ein-Gal | A61N 7/00 |
| | | | 601/4 |
| 2015/0231414 A1* | 8/2015 | Ein-Gal | A61N 7/00 |
| | | | 601/2 |
| 2018/0221688 A1 | 8/2018 | Cioanta | |
| 2018/0296383 A1* | 10/2018 | Blanche | A61F 5/41 |

* cited by examiner

FIG. 1A    FIG. 1B

PRIOR ARTS

500 at an extracorporeal shock wave apparatus comprising a housing, a cavity bound by the housing, an opening in the housing, a plurality of shock wave generators disposed on a first surface of the housing, and a coupling assembly covering the plurality of shock wave generators disposed over the plurality of shock wave generators such that the plurality of shock wave generators are sandwiched by the first surface of the housing and the coupling assembly ~ 502
/ 504 housing has a substantially cylindrical shape
/ 506 housing has a first portion having a substantially cylindrical shape and a second portion having a shape of a frustum, the frustum has a first base with a first circumference and a second base with a second circumference greater than the first circumference, the first portion and the second portion are connected at the first base of the second portion
/ 508 the shock wave generators include a plurality of piezoelectric ceramics disposed on the second side of the housing the shock wave generators include a plurality of conductive wire segments sandwiched by the first surface of the housing and a conductive film each conductive wire segment includes a turn in the conductive wire wound in the shape of a coil
~ 510
\ 512 the coupling assembly includes a sac disposed on the second surface of the housing, the sac configured to contain a quantity of liquid
/ 514 sac is configured to deform in accordance with the volume of liquid contained in the sac, the volume is between a minimum percentage of a volume of the cavity and a maximum percentage of the volume of the cavity
/ 516

ACOUSTIC SHOCK WAVE DEVICES AND METHODS FOR GENERATING A SHOCK WAVE FIELD WITHIN AN ENCLOSED SPACE

FIELD OF THE INVENTION

This disclosure relates generally to a device for generating acoustic shock waves and, more particularly, to a device configured to generating shock waves within an enclosed space for applications in human and veterinary medical treatment.

BACKGROUND

Shock waves are propagating pressure pulses in elastic media, such as air, water and human/animal tissue. Acoustic shock waves have been used for various medical purposes as a noninvasive and non-surgical treatment. It has been proven to be effective to treat a variety of medical conditions in various clinical practices and research reports. For example, in urology, high-intensity focused shock waves are used for breaking kidney/bladder/urethra stones into small fragments on the order of several millimeters in diameter (i.e., lithotripsy), so that the small pieces can be transported out of the patient's body through the urethra. In orthopedics, shock waves are used for pain and inflammation relief/curing in joints and healing of bones. It is also shown that shock wave therapy is effective for healing wound, revascularization, and Peyronie's disease.

Acoustic shock wave generation is often based on three different mechanisms: electrohydraulic, electromagnetic, and piezoelectric. In the electrohydraulic method, a pulse electric discharge between two closely positioned electrodes inside water induces a sudden vaporization of small amount of water nearby. This rapid increase of volume caused by the vaporization creates a pressure pulse in the water, thus generates radial propagating shock waves. In the electromagnetic method, an electric current pulse in a conductor coil results in a pulsed electromagnetic field, which in turn repels a conductive film having certain elastic properties and positioned closely to the coil, thereby generating a momentary (e.g., pulsed) displacement in the conductive film. The momentary displacements in turn generate shock waves with wave fronts parallel to the metal film surface. Alternatively, in the piezoelectric shock wave generation method, electrical voltage pulses are applied to an array of piezoelectric ceramic tiles. The voltage pulses induce volume expansions and contractions of the ceramics with each, thereby generating shock waves with wave fronts parallel to the ceramic surfaces.

Figure 1A:
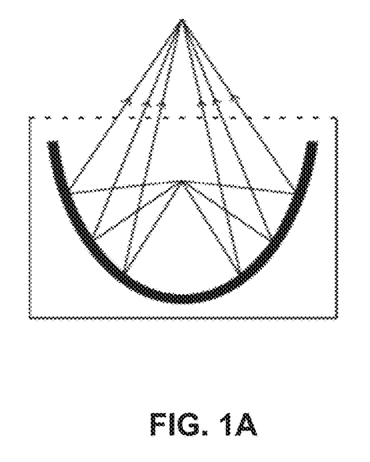
FIGS. 1A-B are schematic illustrations of prior arts of devices for shock wave generation with point source focusing output and point source planar output, respectively.
Figure 1B:
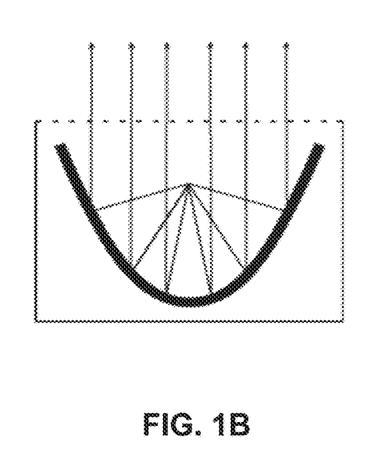

For all the three different methods, the original designs of the shock wave generators are targeting one or more focal points or a focal volume. This is realized utilizing either reflection of a radial (electrohydraulic) wave by an ellipsoidal surface to redirect the waves, or generation directly from a partial spherical surface generator (electromagnetic or piezoelectric). There is also prior design for generating plane wave or nearly plane wave by reflecting using a parabolic surface. All these prior arts share a key feature that the shock wave transducers have a window through which shock waves are emitted, and this window is opened towards a specific direction regardless of convergent or divergent shock waves. Considering the energy flow of the shock waves for the prior arts, the shock wave energy is exiting the window and propagating away from the window towards the target. For example, FIG. 1A shows a focusing device with a point source (usually realized using electrohydraulic method) located in one focal point of an ellipsoid. The radial generated shock waves are reflected by the ellipsoidal surface and become focused on the other focal point of the ellipsoid outside an exit window of the generator. FIG. 1B shows a device for generating planar shock wave by reflecting the shock waves generated by a point source using a parabolic curved surface. By modifying the shape of the reflection surface or the shape of the surface generator, the shock wave emission can be changed from convergent to divergent. These are all described in prior arts. All the prior arts have a share feature, which is an exit window and a certain direction of transmission regardless of convergent, divergent, or planar.

SUMMARY OF THE INVENTION

The prior art designs are well-suited for treating small target (e.g., lithotripsy), but they fail to fulfill the need for treating homogeneously and simultaneously large target areas and volumes, such as a human or animal body appendage, which is important in many new low-intensity medical or veterinarian applications. There is a need for a device that optimizes generation of a shock wave field within an enclosed space filled by a whole or part of human/animal organ, so that the whole volume of the organ or part of the organ can be treated by the shock wave simultaneously, and substantially homogenously. Such a device should preferably generate shock wave field within a cavity for different parts of the body. Such a device would reduce the time for treatment and improve consistency of efficacy, since it avoids the extensive scanning when using a source with directed shock waves.

Some aspects of the present disclosure provide a device for generating an acoustic shock wave field within a cavity. In some aspects of the disclosure, the shock wave device optionally includes a housing having a cylindrical portion and a cone frustum portion. In some embodiments, the housing optionally forms a cavity configured to receive a body appendage. The shock wave device optionally includes a plurality of shock wave generators. In some embodiments, the plurality of shock wave generators optionally include a combination of a conductive thin film and a plurality of conductive wire segments sandwiched by the conductive thin film and the housing, where the conductive thin film and the conductive wire segments are insulated from each other. In some embodiments, the plurality of shock wave generators optionally include a plurality of piezoelectric ceramics disposed on an inner surface of the housing. In some embodiments, the shock wave device optionally includes a coupling assembly disposed over the plurality of shock wave generators. In some embodiments, the coupling assembly optionally has a deformable sac configured to hold shock wave transmitting liquid. The volume of the transmitting liquid is optionally increased or decreased as needed so that the coupling assembly can conform to the shape of the body appendage.

In some aspects of the disclosure, the shock waves generated optionally has an intensity gradient (e.g., non-uniform intensity) within the cavity of the shock wave device by using different shock wave generators, changing the placement of the shock wave generators, or varying an electrical signal that is sent to the shock wave generators. In some embodiments, the intensity gradient is optionally controllable using a control and power supply unit.

The various aspects of the present disclosure provide devices and method that can confine the generated shock wave pulses within the cavity and distribute the generated shock waves substantially within the cavity. As a result, the entire desired volume of treatment is immersed in the shock wave field, and the entire volume can be treated simultaneously. This would significantly improve shock wave treatment efficiency and consistency of efficacy, since it obviates the extensive (and often manual) scanning using directed shock wave sources in prior arts. Furthermore, the controllable and adjustable intensity gradient of the shock waves generated using various aspects of the present disclosure offers more customizable treatment options for various indications and severities, thereby making the shock wave therapy more effective.

DETAILED DESCRIPTION OF EMBODIMENTS

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

Figure 2A:
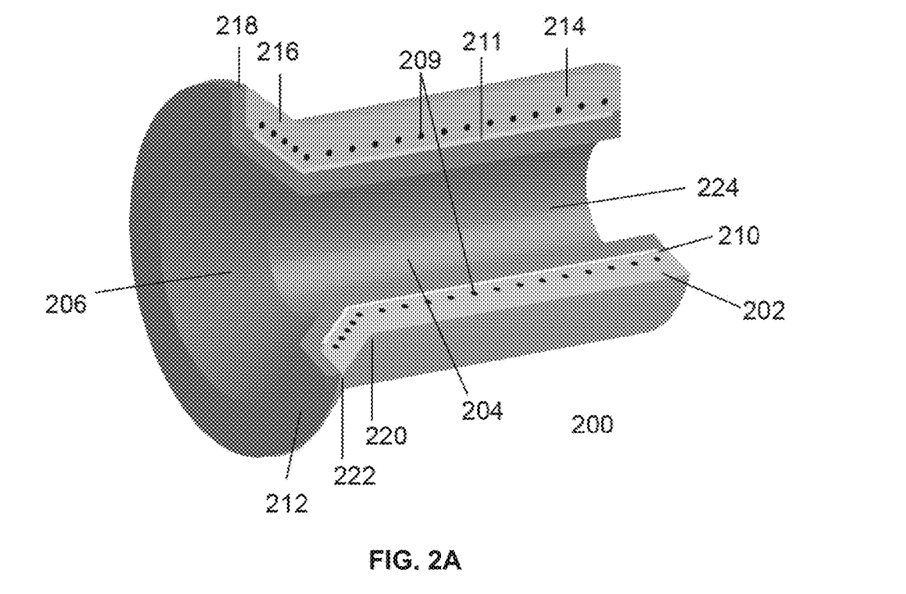
FIGS. 2A-2B illustrate an exemplary shock wave device 200 according to various aspects in the present disclosure.
Figure 2B:
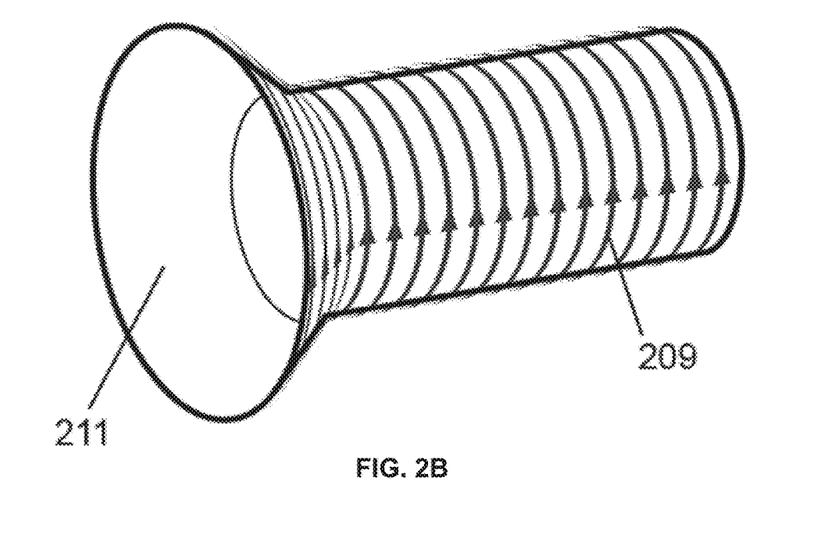

FIGS. 2A-2B illustrate an exemplary shock wave device 200 according to various aspects of the present disclosure. The device 200 includes a housing 202 that has a substantially cylindrical portion 214 and a cone frustum portion 216, as well as an inner surface 210 that expands to both the cylindrical portion 214 and the cone frustum portion 216. The cone frustum portion 216 of the housing has a smaller circumference 220 and a larger circumference 222. Device 200 further includes a cavity 204 bound by the housing 202 and a first opening 206 in the housing that gives access to the cavity 204. In some embodiments, device 200 further includes a second opening 224 on the opposite side of the first opening 206. In some embodiments, the housing is optionally manufactured using various suitable materials generally known in the art, such as metal or plastic; the housing is optionally manufactured using production processes generally known in the art, such as injection molding, Computer Numerical Control (CNC) subtractive machining, or computerized additive manufacturing (i.e., 3-D Printing). Shock wave device 200 further includes multiple electromagnetic shock wave generators: specifically, multiple turns of a conductive wire coil 209 sandwiched between a conductor film 211 and the housing 202. The multiple electromagnetic shock wave generators (209 and 211) are located on at least a substantial portion of the inner surface 210 of the housing 202, so that shock waves originate from a substantial area of the three-dimensional surface defined by the housing 202. In some preferred embodiments, as illustrated in FIGS. 2A-2B, the multiple electromagnetic shock wave generators are located throughout substantially all of the inner surface 210 of the housing 202. Each shock wave generator (e.g., the combination of each turn of a conductive wire coil 209 and the conductor film 211) is configured to generate a shock wave propagating within the cavity 204: when a pulsed electric current is applied in the coil (e.g., 209, shown in FIG. 2B together with conductive thin film 211 without showing the housing), an electromagnetic field with pulsed energy is generated. Notably, the pulsed electromagnetic field is significantly different from a static magnetic field that could be generated by this coil with a constant flowing electric current. Based on Maxwell's equations, a rapidly changing magnetic field in time would generate electric field, and the generated electric field would also generate magnetic field since it is changing rapidly, too. Therefore, the electromagnetic field generated by the pulsed current in the coil is a complex electromagnetic field which expels the metal thin film to make a sudden elastic displacement. Such displacement results in a pressure pulse and generates an inward propagating shock wave. Device 200 also includes a coupling assembly 212, which includes an inflatable sac (218).

Figure 2C:
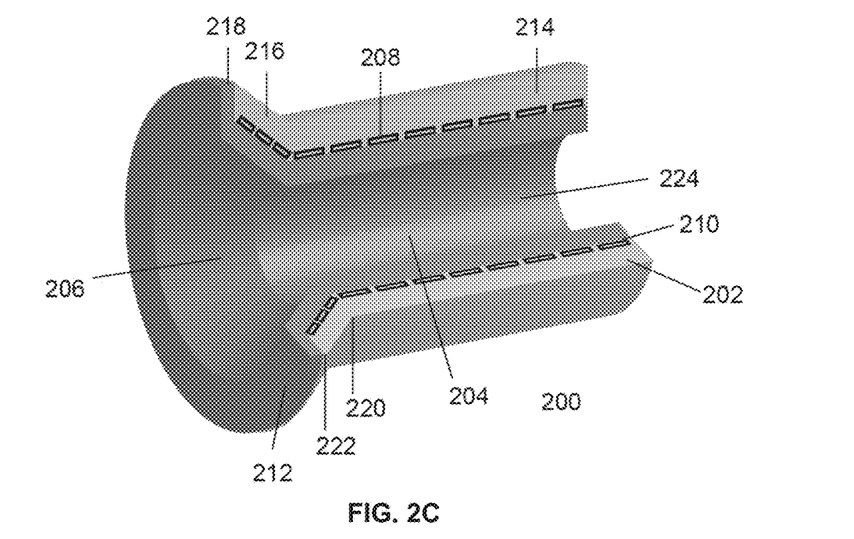
FIGS. 2C-2D illustrate another exemplary shock wave device 200 according to various aspects in the present disclosure.
Figure 2D:
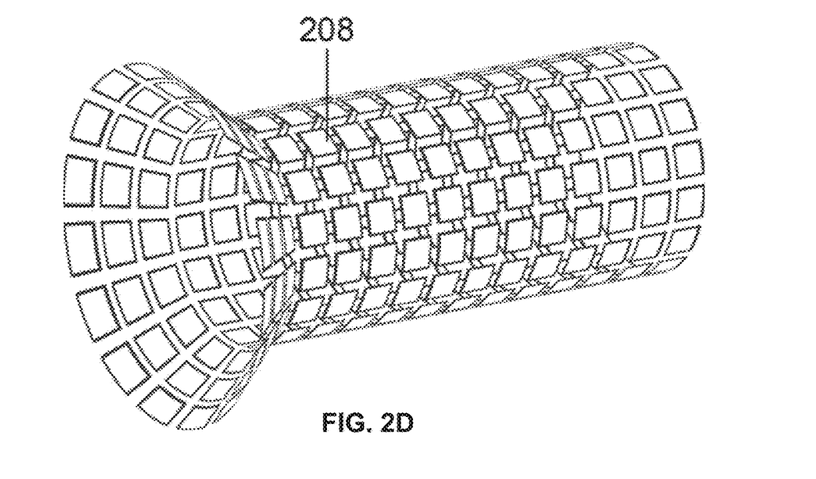

FIGS. 2C-2D illustrate another exemplary shock wave device 200 according to various aspects of the present disclosure. The device 200 includes a housing 202 that has a substantially cylindrical portion 214 and a cone frustum portion 216, as well as an inner surface 210 that expands to both the cylindrical portion 214 and the cone frustum portion 216. In some embodiments, device 200 further includes a second opening 224 on the opposite side of the first opening 206. The cone frustum portion 216 of the housing has a smaller circumference 220 and a larger circumference 222. In some embodiments, the housing is optionally manufactured using various suitable materials generally known in the art, such as metal or plastic; the housing is optionally manufactured using production processes generally known in the art, such as injection molding, Computer Numerical Control (CNC) subtractive machining, or computerized additive manufacturing (i.e., 3-D Printing). Device 200 further includes a cavity 204 bound by the housing 202 and a first opening 206 in the housing that gives access to the cavity 204. Shock wave device 200 further includes multiple piezoelectric ceramic tile shock wave generators 208 disposed on the inner surface 210 of the housing 202. The multiple electromagnetic shock wave generators 208 are located on at least a substantial portion of the inner surface 210 of the housing 202, so that shock waves originate from a substantial area of the three-dimensional surface defined by the housing 202. In some preferred embodiments, as illustrated in FIGS. 2A-2B, the multiple electromagnetic shock wave generators are located throughout substantially all of the inner surface 210 of the housing 202. Piezoelectric ceramics square tiles 208 (shown as example) are disposed on the inner surface 210 of the housing 202. A pulsed signal can be applied to any of the piezoelectric tiles and cause sudden expansion and contraction of the tile, thereby generating a pressure pulse. Device 200 also includes a coupling assembly 212, which includes an inflatable sac (218).

Figure 3A:
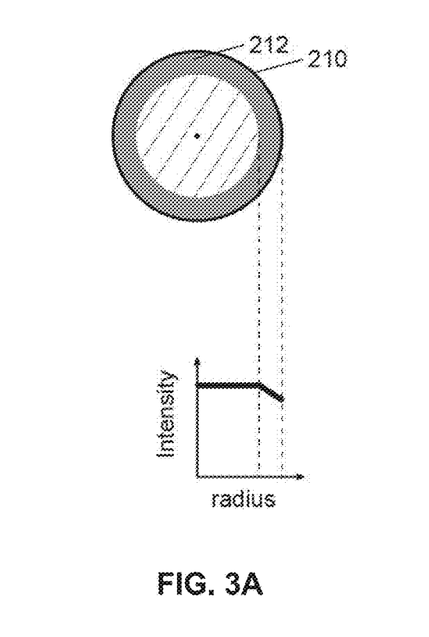
FIGS. 3A-3B illustrate exemplary shock wave intensity gradients generated by exemplary shock wave devices according to various aspects of the present disclosure.
Figure 3B:
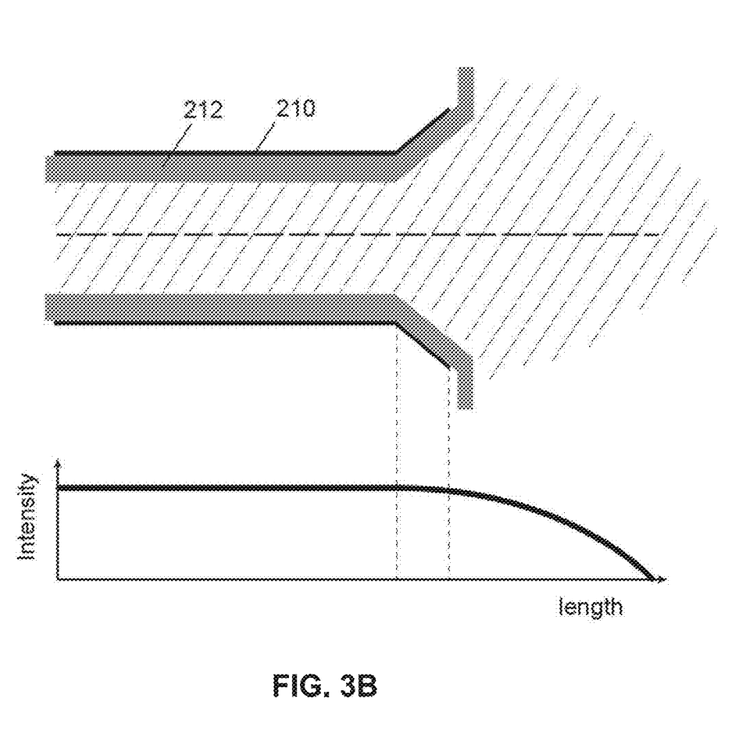

FIGS. 3A-3B illustrate exemplary shock wave intensity gradients generated by exemplary shock wave devices according to various aspects of the present disclosure. FIG. 3A illustrates an exemplary shock wave intensity as a function of the distance from the radial axis of the shock wave generator device. The intensity here is defined as shock wave energy density. The exemplary shock wave intensity as show in FIG. 3A is substantially uniform as a function of distance from the radial axis within the cavity filled by human or animal tissue (not shown) for treatment, while the intensity is lower in the coupling assembly 212 (e.g., all or substantially all of the shock wave energy generated by the shock wave device is consumed within the treated human or animal tissue). This can be realized due the following reasons. Due to geometry effect and conservation of energy, shock wave energy density should be higher approaching the center of the volume. Yet this intensification is optionally compensated by the decay of energy from the energy consumption for the treatment of the tissue. This compensation optionally homogenizes energy density within the treated volume. In some embodiments, as illustrated in FIG. 3B, the housing (e.g., 210) of an exemplary shock wave device includes a cylindrical portion and a cone frustum portion, and all or substantially all of the shock wave energy generated by shock wave generators (not shown) disposed in the cylindrical portion of the shock wave device is uniformly or substantially uniformly (e.g., the intensity along the length is uniform or substantially uniform) contained in the cylindrical portion of the device. Furthermore, as illustrated in FIG. 3B, the intensity of shock waves generated by shock wave generators in the cone frustum portion of the housing optionally decreases due to the angular shape of the cone frustum portion of the housing (e.g., an non-uniform intensity gradient exists in the generated shock wave field). The angular shape of the cone frustum portion also causes shock waves generated by shock wave generators disposed on the cone frustum portion to reach further than the length of the housing on the cone frustum end (e.g., FIG. 3B), thereby advantageously enabling generated shock waves to treat an area of the body that connects to a body appendage. For example, where the treated body appendage is a penis, the corpus spongiosum of a penis extends length-wise from the visible portion of the penis shaft into the body; shock waves having an intensity gradient as illustrated in FIG. 3B can reach both the portion of the corpus spongiosum in the visible penis shaft and the portion in the body, thereby increasing the treatment efficacy and reducing treatment time.

Figure 4:
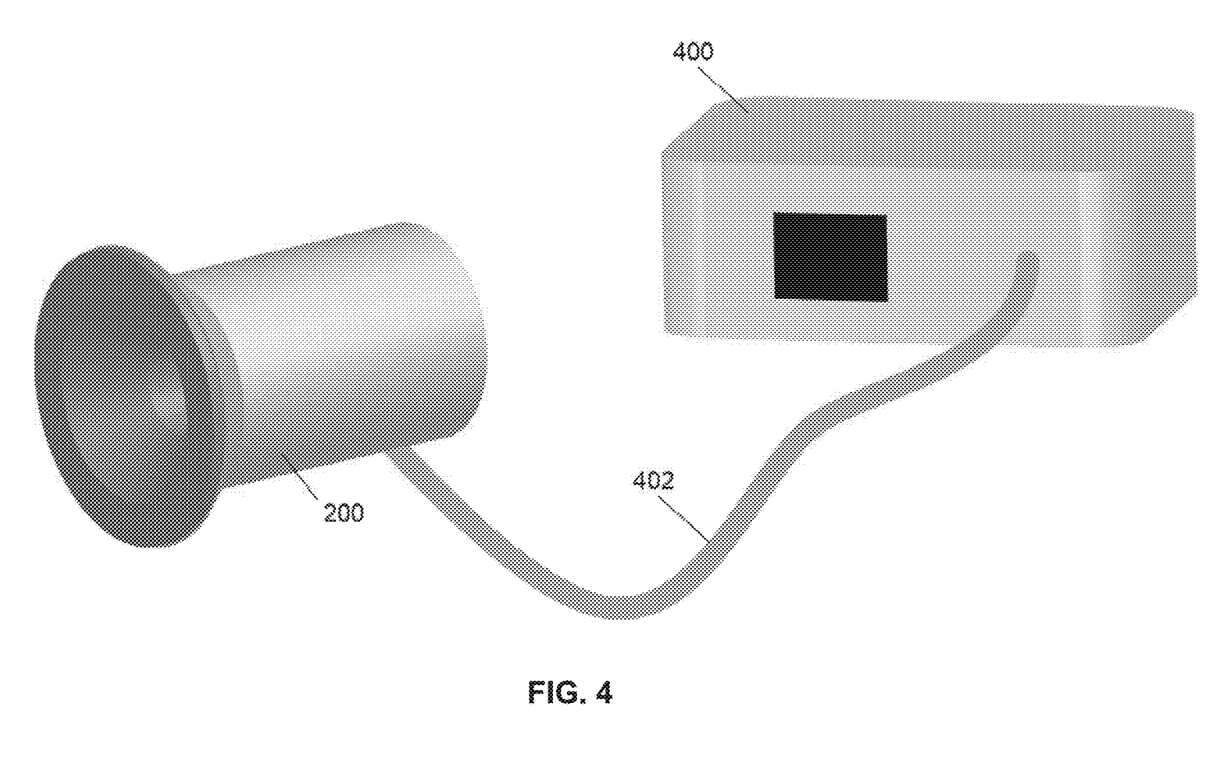
FIG. 4 illustrates an exemplary shock wave device with a control and power supply unit according to various aspects of the present disclosure.

FIG. 4 illustrates an exemplary shock wave device with a control and power supply unit according to various aspects of the present disclosure. The control and power supply unit 400 is configured to connect electrically to the shock wave generators (e.g., 208 or 209 and 211) via a connection line 402 in order to provide a pulsed electrical signal (e.g., an pulsed voltage or a pulsed current) to the shock wave generators. In some embodiments, the control and power supply unit 400 optionally controls the shock wave generators by sending multiple control signals, where each control signal controls a subset of the shock wave generators (e.g., a first control signal controls shock wave generators disposed on the cylindrical portion of the housing (e.g. 214) and a second control signal controls shock wave generators disposed on the cone frustum portion of the housing (e.g., 216). In some embodiments, the control and power supply unit optionally includes one or more user-selectable settings that adjust the intensity of shock wave pressure pulses produced by a group of the shock wave generators by, for example, adjusting the pulse amplitude, pulse width, pulse repetition rate, or pulse delay (e.g., phase) of the pulse voltage signal or the pulse current signal.

The control and power supply unit 400 optionally controls the inflation and deflation of the deformable sac 218 in the coupling assembly 212 by filling the deformable sac with shock wave transmission fluid or draining shock wave transmission fluid from the deformable sac via the connection line 402. In some embodiments, the control and power supply unit 400 optionally includes one or more voltage or current-pulse generating circuitry (e.g., switch capacitors, voltage transformers, diode rectifiers, clock signal generators, isolators, and other electronic circuitry and components generally known in the arts) configured to generate a pulsed voltage signal, a pulsed current signal, or both. In some embodiments, the control and power supply unit 400 optionally includes one or more user-selectable settings that adjust e.g., the magnitude, duration, repetition period, and other parameters of the pulsed signal (e.g., voltage or current). In some embodiments, the control and power supply unit optionally includes one or more user-selectable settings that adjust the amount of shock wave transmission fluids in the sac. In some embodiments, one or more pressure sensors (e.g., Piezoresistive, Capacitive, Piezoelectric, Micro Electro-Mechanical System (MEMS), or other types of pressure sensors generally known in the art) are optionally disposed on or within the coupling assembly (e.g., 212) and configured to sense the pressure of the sac pressing against the body appendage by sensing the pressure of the shockwave transmission liquid as the sac is being filled with the shockwave transmission liquid. In some embodiments, the control and power supply unit optionally receives an electrical signal transmitted from the one or more pressure sensors corresponding to a measured pressure value from the coupling unit and, in accordance with the measure pressure, stops filling the sac with shock wave transmission liquid.

Various aspects of the present disclosure include an extracorporeal shock wave apparatus (e.g., 200). In some embodiments, the apparatus includes a housing (e.g., 202) configured to enclose a body appendage. In some embodiments, the apparatus (e.g., 200) optionally includes a cavity (e.g., 204) bound by the housing, the housing further comprising a first opening (e.g., 206) configured to receive the body appendage into the cavity. In some embodiments, the body appendage is optionally a finger, an arm, a leg, a foot, or a head. In some embodiments, the body appendage is optionally a penis. In some embodiments, the cavity or the housing optionally have dimensions and shapes that are slightly larger than the typical size of the body appendage to be inserted; thus, In some embodiments where the apparatus is intended to enclose a penis, the cavity optionally has a size (e.g., width, length, diameter, etc.) slightly larger than the typical size of a penis.

In some embodiments, the apparatus optionally includes a plurality of shock wave generators (e.g., 208) disposed on a first surface (e.g., inner surface 210) of the housing (e.g., the side facing the cavity), each shock wave generator configured to generate a shock wave propagating within the cavity. In some embodiments, the plurality of shock wave generators are placed uniformly; that is, each of the plurality of shockwave generators is optionally separated by the same distance from another shock wave generator.

In some embodiments, the apparatus optionally includes a coupling assembly (e.g., 212) that is disposed over the plurality of shock wave generators (e.g., 208) such that the plurality of shock wave generators are sandwiched by the first surface of the housing (e.g., inner surface 210) and the coupling assembly. In some embodiments, the coupling assembly is optionally created using methods generally known in the art such as adhesives, retainers, etc. In some embodiments the coupling assembly is optionally detachable, that is, the coupling assembly can be repeatedly removed from and re-attached inside the cavity, covering the plurality of shock wave generators disposed on the inside surface of the housing. In some embodiments, the coupling assembly is optionally configured to transmit the plurality of shock waves to the body appendage. In some embodiments, the coupling assembly optionally includes a medium that transmits shockwave pressure pulses with less intensity decay than air. Notably, a shock wave device according to various embodiments of the present invention can confine the generated shock wave pulses within the cavity and distribute the generated shock waves substantially within the cavity. As a result, the entire desired volume of treatment is immersed in the generated shock waves, and the entire volume can be treated simultaneously. This would significantly improve shock wave treatment efficiency and consistency of efficacy, and reducing treatment time, since it obviates the extensive (and often manual) scanning using directed shock wave sources in prior arts.

In some embodiments, the housing (e.g., 202) optionally has a substantially cylindrical shape. That is, in some embodiments, the housing optionally has a circular or substantially circular cross-section. In some embodiments, the housing optionally has an elongated length (e.g., the shape of a shaft). In some embodiments, the housing (e.g., 202) optionally has a first portion (e.g., 214) having a substantially cylindrical shape and a second portion (e.g., 216) having a shape of a cone frustum, where the cone frustum has a first base with a first circumference (e.g., 220) and a second base with a second circumference greater than the first circumference (e.g., 222), and where the first portion (e.g., 214) and the second portion (e.g., 216) are connected at the first base (e.g., 220). Notably, a shock wave device whose housing includes both a cylindrical-shaped portion and a frustum-shaped portion can enclose and deliver shock waves to both the portion of the body appendage protruding from the torso and any portion of the body appendage within the torso, thereby increasing treatment efficiency and efficacy and reducing treatment time.

In some embodiments, the plurality of shock wave generators optionally includes a plurality of piezoelectric ceramic tiles (e.g., 208) disposed on the inner surface of the housing. In some embodiments, the piezo electric ceramic tiles are optionally round, oval, hexagonal, rectangular, square, or other shapes generally known in the art. In some embodiments, piezoelectric ceramic tiles (e.g., 208) with different sizes and shapes are optionally installed at various locations on the inner surface (210) of the housing (202) (including, e.g., the inner surface of the second (cone frustum) portion (e.g., 216) of the housing) to create a wave field having an intensity gradient. In some embodiments, the plurality of piezoelectric ceramic tiles are optionally connected to the power supply and control unit using one or more electrical connection devices such as wires, flexible printed circuits, and embedded printed metal traces, as well as other electrical connection devices generally known in the art. In some embodiments, one or more holes are optionally embedded in the housing in order to pass electrical connection from outside the housing to the shock wave generators.

In some embodiments, the plurality of shock wave generators optionally includes a plurality of conductive wire segments (e.g., 209) sandwiched by (e.g., fitting snugly between) the housing and a conductive film (e.g., 211). In some embodiments, the plurality of conductive wire segments (e.g., 209) are electrically insulated from the conductive film (e.g. 211). The plurality of wire segments are optionally configured to transmit an electrical signal, and the conductive film (e.g., 211) are optionally configured to momentarily deform in response to an electromagnetic field generated by the electrical signal in the plurality of conductive wire segments. In some embodiments, the conductive wire or trace segments optionally include one continuous wire disposed on the inner surface of the housing. In some embodiments, the wire or trace segments optionally have one or more of the following layout shapes: serpentine (e.g., electrical current in two neighboring segments run in the opposite directions), or angular (e.g., neighboring trace segments are neither parallel nor perpendicular with each other).

In some embodiments, each conductive wire segment (e.g., 209) optionally includes a turn in the conductive wire or trace, the conductive wire or trace wound in the shape of a coil. In other words, electrical current in two neighboring wire or trace segments run in the same direction. In some embodiments each turn of the conductive coil is optionally separated from its nearest neighboring coil turn by the same distance (e.g., the conductive wire coil is wound with a constant winding density). In some embodiments, each turn in the conductive wire is optionally connected to its two neighboring wire segments. In some embodiments, the conductive wire segments are optionally formed by one continuous conductive wire or trace. In some embodiments, the distance between two neighboring coil turns may be different (e.g., the winding density of the conductive wire coil varies). Varying the winding density (e.g. the distance between neighboring conductive wire segments) optionally enables changing the intensity gradient of the generated shock wave without needing to vary the electrical signal from the power supply and control unit (e.g., 400). In some embodiments, each conductive wire or trace segment is optionally not connected with the neighboring wire or trace segments; in other words, each turn in the conductive wire or trace is optionally connected directly to the control and power supply unit through a corresponding electrical connection not shared with another turn of conductive wire or trace. Such a design allows the control and power supply unit to control individually the intensity of the shock wave generated by each turn of conductive wire or trace, thereby forming a shock wave field with an intensity gradient, which can selectively deliver shockwaves of varying intensities to different parts of the body member under treatment, thereby offering user more customization and control over the treatment.

In some embodiments, the plurality of shock wave generators (e.g., 208) are optionally configured to generate a shock wave field having an intensity gradient, the shock wave field include the corresponding shock waves (pressure pulses) generated by each shock wave generator. In other words, in some embodiments the shock wave pressure pulse generated by each of the plurality of shock wave generators form collectively a shock wave field. In some embodiments the shock wave field optionally has an intensity gradient (e.g., the intensity of the shock wave field is optionally divergent instead of uniform. In some embodiments, the intensity gradient is optionally achieved by varying the placement densities of the shock wave generators on the inner surface of the housing; for example, in exemplary embodiments where the housing (e.g., 202) optionally includes a second portion (e.g. 215) having a shape of a cone frustum, a higher density of a plurality of shock wave generators are optionally disposed on the second (e.g. cone frustum) portion (e.g., the distance separating piezoelectric tiles 208 disposed on the cone frustum portion are smaller than the distance separating piezoelectric tiles disposed on the cylindrical portion, or the distance separating conductive wires 209 disposed on the cone frustum portion are smaller than the distance separating conductive wires disposed on the cylindrical portion). In some embodiments, the intensity gradient is optionally achieved by varying the size of the shockwave generators (e.g., 208) on the inner surface of the housing (e.g., using larger piezoelectric tiles in the cone frustum portion than in the cylindrical portion). In some embodiments, the intensity gradient is optionally achieved by varying the amplitude of an electrical signal (e.g., a pulsed voltage signal in an exemplary embodiment where the plurality of shockwave generators are optionally piezoelectric tiles (e.g., 208), or a pulsed current signal in an exemplary embodiment where the plurality of shockwave generators are optionally conductive wire segments (e.g., 209) and a conductive thin film (e.g., 211). In some embodiments, the intensity gradient is achieved optionally by placing the shock wave generators to create constructive interference to increase intensity at various three-dimensional locations within the cavity, or to create destructive interference to decrease intensity at various three-dimensional locations within the cavity (e.g., 204). In some embodiments the intensity gradient is achieved optionally by using shockwave generators that have varying sizes and shapes. In some embodiments, the intensity gradient is optionally between a minimum intensity and a maximum intensity. In some embodiments, the intensity gradient is optionally between $0.01$ $mJ/mm^2$ per pulse and $0.1$ $mJ/mm^2$ per pulse. In some embodiments, the intensity gradient is optionally between $0.1$ $mJ/mm^2$ per pulse and $0.2$ $mJ/mm^2$ per pulse. In some embodiments, the intensity gradient is optionally between $0.2$ $mJ/mm^2$ per pulse and $0.4$ $mJ/mm^2$ per pulse. In some embodiments, the intensity gradient is optionally between $0.4$ $mJ/mm^2$ per pulse and $4$ $mJ/mm^2$ per pulse.

In some embodiments, each corresponding shock wave optionally has an adjustable intensity. In some embodiments, a subset of the shock wave generators (e.g., 208) optionally generates corresponding shock waves that have a different intensity than the corresponding shock waves generated by the rest of the plurality of shock wave generators. In some embodiments the subset of shock wave generators optionally includes one shock wave generator. In some embodiments, the different levels of intensity are optionally achieved using the controller/power supply unit (e.g., 402). The configurable intensity gradient of the shock waves generated offers more customizable treatment options for various indications and severities, thereby making the shock wave therapy more effective.

In some embodiments, the coupling assembly (e.g., 212) optionally includes a sac (e.g., 218) disposed on the second surface of the housing, the sac configured to contain a volume of liquid. In some embodiments, the sac is optionally made from elastomers such as natural rubber, neoprene rubber, or Thermoplastic Elastomers (TPE). In some embodiments, the shock wave transmitting liquid is optionally saline water, distilled water, or other suitable types of liquids generally known in the art. In some embodiments, the sac is optionally configured to cover substantially the entire length (e.g., axial length of the cylinder portion 214 and optionally the cone frustum portion 216) of the housing. In some embodiments, the sac is optionally configured to inflate inward until the sac touches the body appendage or optionally press against the body appendage at a predetermined pressure. In some embodiments, the predetermined pressure is optionally pre-set by the power supply and control unit (e.g., 400). In some embodiments the predetermined pressure is optionally adjustable at the power supply and control unit. The deformable coupling assembly with the optional sac allows generated shock waves be transmitted more effectively to the body appendage under treatment, thereby increasing the treatment efficacy and reducing treatment time.

In some embodiments, the sac (e.g., 218) is optionally configured to deform in accordance with the volume of liquid contained in the sac. In some embodiments, the sac is optionally configured to cover substantially the entire height of the housing. In some embodiments, the sac is optionally configured to inflate inward (e.g., reducing the cross-sectional diameter of the portion of the cavity in the housing not occupied by the inflated sac), thereby pressing the inward surface of the sac against the body appendage inserted into the cavity. In some embodiments, the minimum volume of liquid the sac is configured to hold is optionally 1%, 5%, 10%, 15%, 20%, 25%, 30%, 35%, 40%, or 45% of the volume of the cavity. In some embodiments, the maximum volume of liquid the sac is configured to hold is optionally 95%, 90%, 85%, 80%, 75%, 70%, 60%, and 65% of the volume of the cavity. In some embodiments, the minimum volume of liquid in the sac is optionally independent from the maximum volume of liquid in the sac; in other words, there is no one-to-one correspondence between the listed minimum volume and the maximum volume of liquid in the sac. In some embodiments, the sac includes optionally a first opening with an inlet/outlet control. In some embodiments, the inlet/outlet control is optionally connected to a tube that fills the sac with or drains from the sac the shock wave transmission liquid. The volume of the liquid b can be adjusted real-time during the operation, so that the sac can be naturally conformed to the body appendage being treated. Additional coupling gel/liquid can be further applied between the sac and the body appendage to improve transmission efficiency.

In some embodiments, the extracorporeal shock wave apparatus optionally includes a control and power supply unit (e.g., 400) configured to connect electrically to the plurality of shock wave generators, the control and power supply unit configured to control the coupling assembly and a group of the plurality of shock wave generators. In some embodiments, the group of the shock wave generators is optionally a subset (including one) of the shock wave generators. In some embodiments the group of the shock wave generators is all of the shock wave generators. In some embodiments, the control and power supply unit optionally generates an electrical control signal to be sent to the shock wave generators. In some embodiments the electrical control signal is optionally a pulse voltage signal to control one or more piezoelectric ceramic tile shock wave generator. In some embodiments, the electrical control signal is optionally a pulse current signal to control a conductive wire segment shock wave generator. In some embodiments, the control and power supply unit optionally includes one or more user-selectable settings that adjust the intensity of shock wave pressure pulses produced by a group of the shock wave generators by, for example, adjusting a magnitude or a phase of the pulse voltage signal or the pulse current signal. In some embodiments the control and power supply unit optionally controls the inflation and deflation of the deformable sac in the coupling assembly by filling the deformable sac with shock wave transmission fluid or draining shock wave transmission fluid from the deformable sac. In some embodiments, the control and power supply unit optionally includes one or more user-selectable settings that adjust the amount of shock wave transmission fluids in the sac. In some embodiments, the control and power supply unit optionally receives an electrical signal corresponding to a measured pressure value from the coupling unit and, in accordance with the measure pressure, stops filling the sac with shock wave transmission liquid. The control unit improves usability of the shock wave device by providing easy ways to adjust the intensity of generated shock waves and the coupling between the shock wave device and the body appendage being treated, thereby making the shock wave therapy more effective.

Figure 5A:
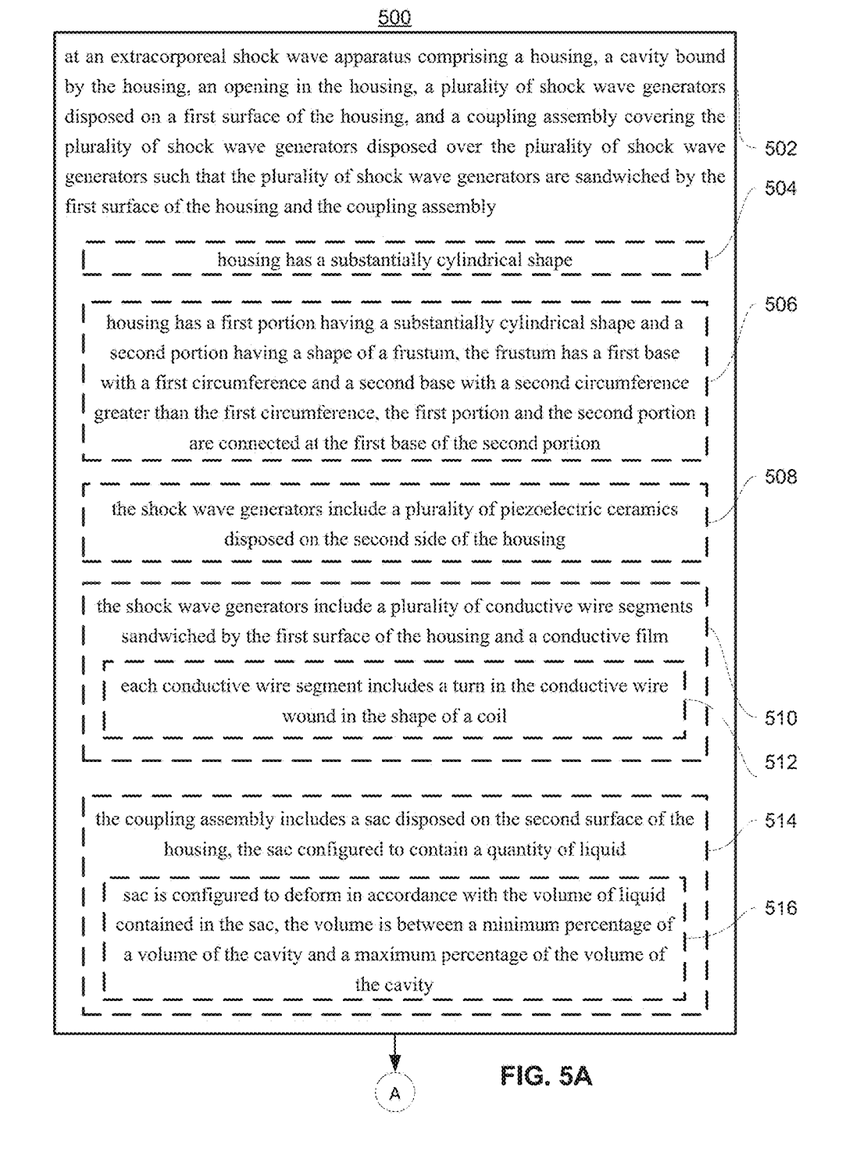
FIGS. 5A-5C illustrate methods of using a shock wave device according to various aspects of the present disclosure.
Figure 5B:
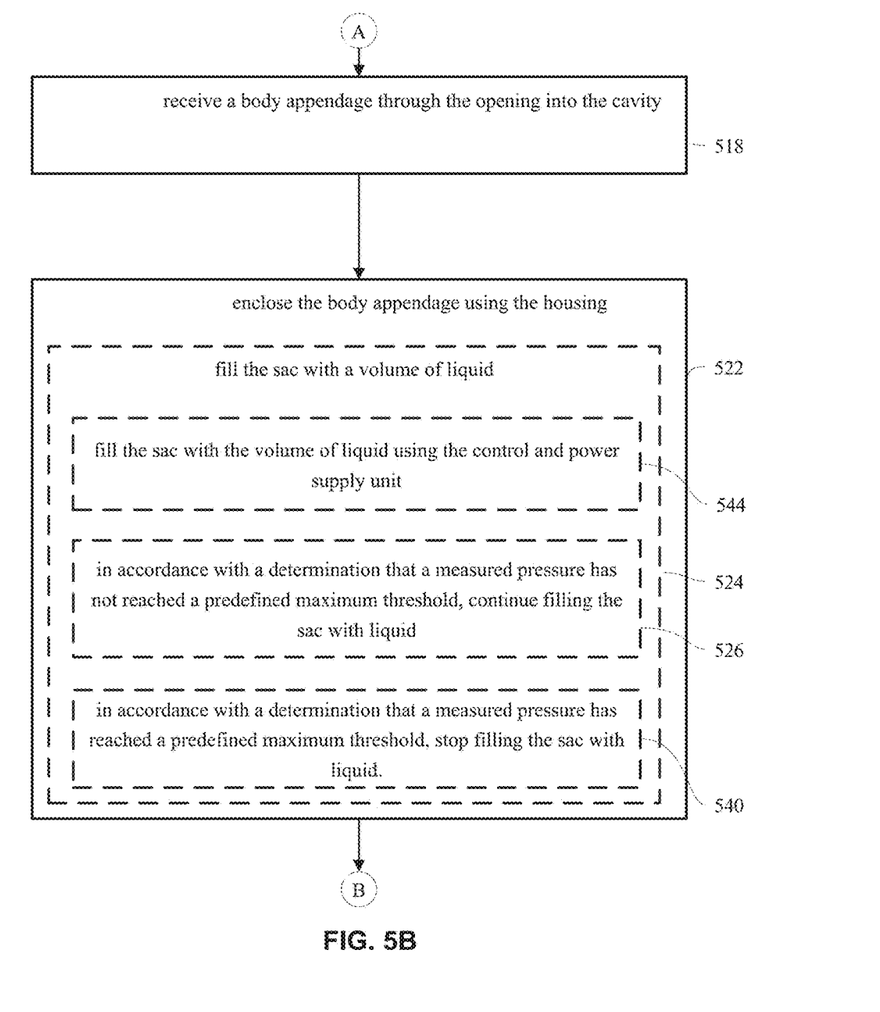
Figure 5C:
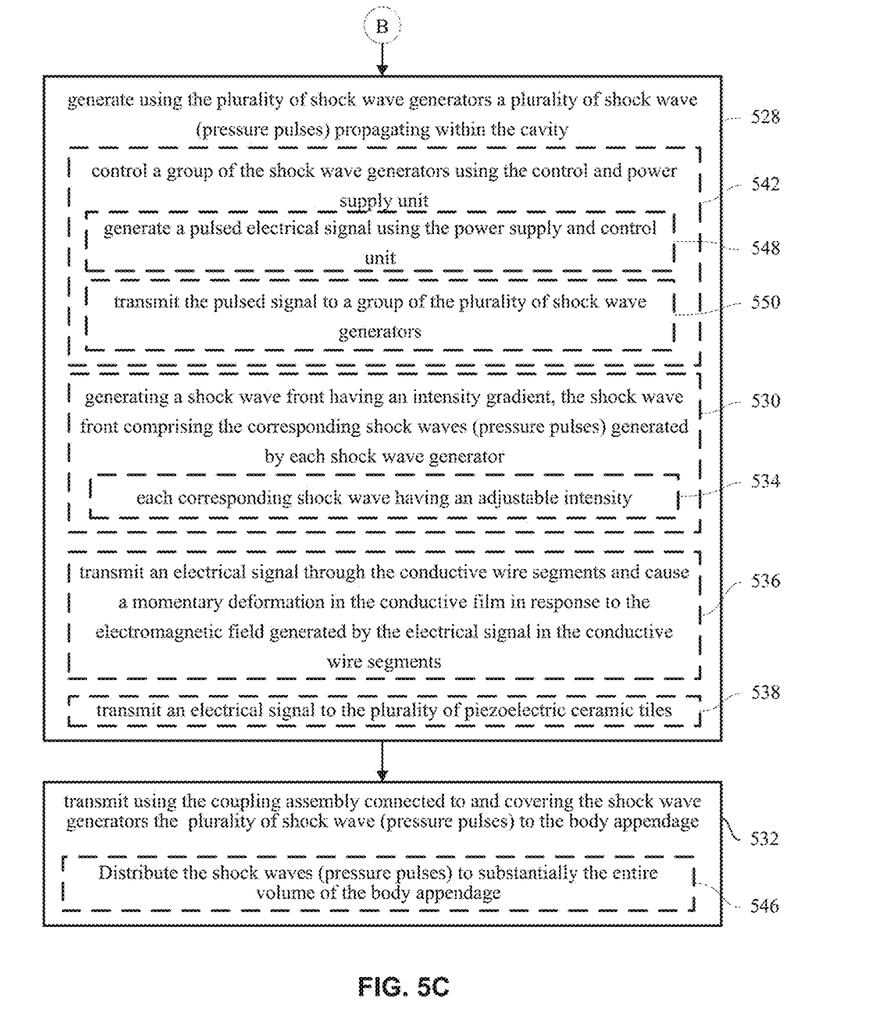

FIGS. 5A-5C illustrate methods of using a shock wave device according to various aspects of the present disclosure. In some embodiments, the method includes (e.g., step 502) using an extracorporeal shock wave apparatus (e.g., 200) that includes a housing (e.g., 202), a cavity (204), a first opening in the housing (e.g., 206), and a plurality of shock wave generators (e.g., 208) disposed on a first surface (e.g., 210) of the housing (e.g., 202), and a coupling assembly (e.g., 212) connected to and covers the plurality of shock wave generators disposed on the first surface of the housing to: receive a body appendage through the first opening into the cavity (e.g., step 518); enclose the body appendage using the housing (e.g., step 522); generate, using the plurality of shock wave generators (e.g., 208), a plurality of shock wave (pressure pulses) propagating within the cavity (e.g., step 528); and transmit, using the coupling assembly connected to and covering the plurality of shock wave generators, the plurality of shock wave (pressure pulses) to the body (e.g., step 532). In some embodiments, transmitting the plurality of shock wave (pressure pulses) to the body appendage optionally includes distributing the plurality of shock wave (pressure pulses) to substantially the entire volume of the body appendage (e.g., step 546).

In some embodiments, the housing disclosed in step 502 optionally has a substantially cylindrical shape (e.g., step 504). In some embodiments, the housing disclosed in step 500 optionally includes a first portion (e.g., 214) having a substantially cylindrical shape and a second portion (e.g., 216) having a shape of a cone frustum, the cone frustum has a first base with a first circumference and a second base with a second circumference greater than the first circumference, and the first portion and the second portion are optionally connected at the first base of the second portion (e.g., step 506).

In some embodiments, the shock wave generators disclosed in step optionally includes (e.g., step 508) a plurality of piezoelectric ceramic tiles (e.g., 208), and the method optionally includes transmitting an electrical signal to the plurality of piezoelectric ceramic tiles (e.g., step 538). In some embodiments, the shock wave generators optionally include (e.g., step 510) a plurality of conductive wire segments (e.g., a turn in the conductive wire wound in the shape of a coil (e.g., 209)) sandwiched by the first surface (e.g., 210) of the housing and a conductive film (e.g., 211), and the method optionally includes transmitting an electrical signal through the conductive wire segments and causing a momentary deformation in the conductive film in response to the electromagnetic field generated by the electrical signal in the conductive wire segments (e.g., step 536).

In some embodiments, the plurality of shock wave generators disclosed in step 502 optionally generates a shock wave field that has an intensity gradient, the shock wave field including the corresponding shock waves (pressure pulses) generated by each shock wave generator (e.g., step 530). In some embodiments each corresponding shock wave optionally has an adjustable intensity (e.g., step 534). In some embodiments, the intensity gradient is optionally between a minimum intensity and a maximum intensity. In some embodiments, the intensity gradient is optionally between 0.01 mJ/mm$^2$ per pulse and 0.1 mJ/mm$^2$ per pulse. In some embodiments, the intensity gradient is optionally between 0.1 mJ/mm$^2$ per pulse and 0.2 mJ/mm$^2$ per pulse. In some embodiments, the intensity gradient is optionally between 0.2 mJ/mm$^2$ per pulse and 0.4 mJ/mm$^2$ per pulse. In some embodiments, the intensity gradient is optionally between 0.4 mJ/mm$^2$ per pulse and 4 mJ/mm$^2$ per pulse.

In some embodiments, the coupling assembly optionally includes (e.g., step 514) a sac (e.g., 218) configured to contain a volume of liquid, and the method optionally includes filling the sac with a volume of liquid (e.g., step 524). In some embodiments, the sac is optionally configured to deform in accordance with the quantity of liquid contained in the sac, and the method optionally includes in accordance with a determination that a measured pressure (e.g., pressure of the liquid in the sac (e.g., 218)) has not reached a predefined maximum threshold, continuing filling the sac with liquid (e.g., step 526). In some embodiments, the method optionally includes in accordance with a determination that the measured pressure (e.g., pressure of the liquid in the sac) has reached a predefined maximum threshold, stopping filling the sac with liquid (e.g., step 540).

In some embodiments, the shock wave apparatus (e.g., 200) optionally includes a control and power supply unit (e.g., 402) configured to connect electrically to the plurality of shock wave generators and the method optionally includes controlling a group of the plurality of shock wave generators (e.g.,) using the power supply and control unit (e.g., step 542). In some embodiments, the method optionally includes filling the sac with the volume of liquid using the control and power supply unit. In some embodiments, controlling a group of the plurality of shock wave generators using the power supply and control unit optionally includes the steps of generating, at the power supply and control unit (e.g., 400), a pulsed electrical signal (step 548) and transmitting the pulsed signal to a group of the plurality of shock wave generators (step 550). In some embodiments the electrical control signal is optionally a pulse voltage signal to control one or more piezoelectric ceramic tile shock wave generator. In some embodiments, the electrical control signal is optionally a pulse current signal to control a conductive wire segment shock wave generator. In some embodiments, the pulsed electrical signal optionally has a first amplitude, a first pulse width, and a first pulse repetition period (PRP). In some embodiments, the control and power supply unit (e.g., 402) optionally generates a second pulsed electrical signal that has a second amplitude, a second pulse width, and a second pulse repetition period, where the second amplitude is optionally different from the first amplitude, the second pulse width is optionally different from the first pulse width, and the second pulse repetition period is optionally different from the first pulse repetition period.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

What is claimed is:

1. A device comprising:
   an extracorporeal shock wave apparatus, wherein the apparatus further comprising:

a housing configured to enclose a body appendage in a cavity bound by the housing, the housing further comprising a first opening configured to receive the body appendage into the cavity;

a plurality of shock wave generators, each shock wave generator configured to generate a shock wave propagating within the cavity, the plurality of shock wave generators comprise a plurality of conductive wire segments, wherein the plurality of conductive wire segments are parts of a single conductive wire wound around and along a substantially cylindrical inner surface of the housing, wherein the single conductive wire is wound around the substantially cylindrical inner surface of the housing such that shock wave energy generated by the plurality of shock wave generators is uniform or substantially uniform along a length of the housing; and a deformable coupling assembly covering the plurality of shock wave generators disposed over the plurality of shock wave generators such that the plurality of shock wave generators being sandwiched by the housing and the coupling assembly, wherein the deformable coupling assembly includes a deformable sac configured to contain shockwave-transmitting liquid;

wherein the coupling assembly is configured to expand in accordance with a volume of the shockwave-transmitting liquid to conform to the circumference of the body appendage enclosed in the cavity, and wherein the coupling assembly is configured to transmit the plurality of shock waves to the body appendage.

2. The device in claim 1, wherein the housing has a substantially cylindrical shape.

3. The device in claim 1, wherein the housing further comprising a first portion having a substantially cylindrical shape and a second portion having a shape of a cone frustum, the cone frustum having a first base with a first circumference and a second base with a second circumference greater than the first circumference, the first portion and the second portion being connected at the first base of the second portion.

4. The device in claim 1, wherein the plurality of shock wave generators are further configured to generate a shock wave field having an intensity gradient, the shock wave field comprising corresponding shock waves pressure pulses generated by each shock wave generator.

5. The device in claim 4, wherein each corresponding shock wave having an adjustable intensity.

6. The device in claim 1, wherein the plurality of conductive wire segments is sandwiched by the housing and a conductive film, the plurality of conductive wire segments configured to conduct an electrical signal, and the conductive film configured to momentarily deform in response to an electromagnetic field generated by the electrical signal in the plurality of conductive wire segments.

7. The device in claim 6, wherein each conductive wire segment of the plurality of conductive wire segments comprises a turn in the conductive wire wound in the shape of a coil.

8. The device in claim 1, wherein the coupling assembly comprising a sac configured to contain a volume of liquid.

9. The device in claim 8, wherein the sac is configured to deform in accordance with the volume of liquid contained in the sac, the volume of liquid being between a minimum percentage of a volume of the cavity and a maximum percentage of the volume of the cavity.

10. The device in claim 1, further comprising a control and power supply unit configured to connect to the plurality of shock wave generators, the control and power supply unit configured to control the coupling assembly and a group of the plurality of shock wave generators.

11. A method comprising:

at an extracorporeal shock wave apparatus comprising a housing, a cavity bound by the housing, a first opening in the housing, a plurality of shock wave generators, wherein the plurality of shock wave generators comprise a plurality of conductive wire segments, wherein the plurality of conductive wire segments are parts of a single conductive wire wound around and along the substantially cylindrical inner surface of the housing and wherein the single conductive wire is wound around the substantially cylindrical inner surface of the housing such that shock wave energy generated by the plurality of shock wave generators is uniform or substantially uniform along a length of the housing, and a deformable coupling assembly disposed over the plurality of shock wave generators such that the plurality of shock wave generators being sandwiched by the housing and the coupling assembly, wherein the deformable coupling assembly includes a deformable sac configured to contain shockwave-transmitting liquid and wherein the coupling assembly is configured to expand in accordance with a volume of the shockwave-transmitting liquid to conform to the circumference of the body appendage enclosed in the cavity:

receiving a body appendage through the first opening into the cavity;

enclosing the body appendage using the housing;

generating, using the plurality of shock wave generators, a plurality of shock wave pressure pulses propagating within the cavity; and transmitting, using the coupling assembly connected to and covering the plurality of shock wave generators, the plurality of shock wave pressure pulses to the body appendage.

12. The method in claim 11, wherein the housing has a substantially cylindrical shape.

13. The method in claim 11, wherein the housing further comprising a first portion having a substantially cylindrical shape and a second portion having a shape of a cone frustum, the cone frustum having a first base with a first circumference and a second base with a second circumference greater than the first circumference, the first portion and the second portion being connected at the first base of the second portion.

14. The method in claim 11, wherein generating a plurality of shock wave pressure pulses propagating within the cavity further comprising generating a shock wave field having an intensity gradient, the shock wave field comprising corresponding shock waves pressure pulses generated by each shock wave generator.

15. The method in claim 14, wherein each corresponding shock wave having an adjustable intensity.

16. The method in claim 1, wherein the plurality of conductive wire segments are sandwiched by the inner surface of the housing and a conductive film, the method further comprising:

transmitting an electrical signal through the plurality of conductive wire segments; and causing the conductive film to momentarily deform in response to an electromagnetic field generated by the electrical signal in the plurality of conductive wire segments.

17. The method in claim 16, wherein each conductive wire segment of the plurality of conductive wire segments comprises a turn in the conductive wire wound in the shape of a coil.

18. The method in claim 11, wherein the coupling assembly comprising a sac disposed on the second surface of the housing, the sac configured to contain a volume of liquid, the method further comprising: filling the sac with the volume of liquid.

19. The method in claim 18, wherein the sac is configured to deform in accordance with the volume of liquid contained in the sac, the method further comprising:
    in accordance with a determination that a measured pressure has not reached a predefined maximum threshold, continuing filling the sac with the liquid; and
    in accordance with a determination that the measured pressure has reached the predefined maximum threshold, stopping filling the sac with the liquid.

20. The method in claim 19, wherein the apparatus further comprising a control and power supply unit configured to connect electrically to the plurality of shock wave generators, wherein filling the sac comprises:
    controlling a group of the plurality of shock wave generators using the power supply and control unit; and
    filling the sac with the volume of liquid using the control and power supply unit.

21. The method in claim 20, wherein controlling the group of the plurality of shock wave generators using the power supply and control unit further comprising:
    generating, at the power supply and control unit, a pulsed electrical signal; and
    transmitting the pulsed signal to the group of the plurality of shock wave generators.

22. The method of claim 11, wherein transmitting the plurality of shock wave to the body appendage includes distributing the plurality of shock wave to substantially the entire volume of the body appendage.

* * * * *